(12) United States Patent
Brown

(10) Patent No.: US 12,115,392 B2
(45) Date of Patent: Oct. 15, 2024

(54) GATING OF RADIOTHERAPY

(71) Applicant: Elekta Limited, Crawley (GB)

(72) Inventor: Kevin Brown, Crawley (GB)

(73) Assignee: Elekta Limited, Crawley (GB)

( * ) Notice: Subject to any disclaimer, the term of this patent is extended or adjusted under 35 U.S.C. 154(b) by 423 days.

(21) Appl. No.: 17/594,858

(22) PCT Filed: May 1, 2020

(86) PCT No.: PCT/EP2020/062219
§ 371 (c)(1),
(2) Date: Nov. 1, 2021

(87) PCT Pub. No.: WO2020/221931
PCT Pub. Date: Nov. 5, 2020

(65) Prior Publication Data
US 2022/0288420 A1 Sep. 15, 2022

(30) Foreign Application Priority Data

May 2, 2019 (GB) ..................................... 1906176

(51) Int. Cl.
*A61N 5/10* (2006.01)

(52) U.S. Cl.
CPC ......... *A61N 5/1068* (2013.01); *A61N 5/1037* (2013.01); *A61N 5/1049* (2013.01); *A61N 5/1071* (2013.01); *A61N 2005/1055* (2013.01); *A61N 2005/1072* (2013.01)

(58) Field of Classification Search
None
See application file for complete search history.

(56) References Cited

U.S. PATENT DOCUMENTS

| | | | |
|---|---|---|---|
| 5,373,844 A | 12/1994 | Smith et al. | |
| 6,530,873 B1 | 3/2003 | Lee | |
| 2012/0271094 A1 | 10/2012 | Fuller | |
| 2019/0054320 A1* | 2/2019 | Owens | A61N 5/1071 |
| 2020/0306559 A1* | 10/2020 | Kuusela | A61N 5/1043 |

FOREIGN PATENT DOCUMENTS

EP 0940158 A1 9/1999

OTHER PUBLICATIONS

"European Application Serial No. GB1906176.1, Search Report and Examination Report mailed Oct. 29, 2019", (Oct. 29, 2019), 5 pgs.
"International Application Serial No. PCT/EP2020/062219, International Search Report mailed Jun. 9, 2020", (Jun. 9, 2020), 5 pgs.
"International Application Serial No. PCT/EP2020/062219, Written Opinion mailed Jun. 9, 2020", (Jun. 9, 2020), 7 pgs.

* cited by examiner

*Primary Examiner* — Hoon K Song
(74) *Attorney, Agent, or Firm* — Schwegman Lundberg & Woessner, P.A.

(57) ABSTRACT

A radiotherapy device, a method and a computer readable medium are disclosed. The radiotherapy device includes a radiation source and a controller. The radiation source is configured to apply radiation to a subject. The controller is configured to determine an overlap between a defined volume of the subject and an isodose surface and to instruct the radiation source to halt application of the radiation based on the determination.

18 Claims, 8 Drawing Sheets

GATING OF RADIOTHERAPY

PRIORITY APPLICATIONS

This application is a U.S. National Stage Filing under 35 U.S.C. § 371 from International Application No. PCT/EP2020/062219, filed on May 1, 2020, and published as WO2020/221931 on Nov. 5, 2020, which claims the benefit of priority to United Kingdom Application No. 1906176.1, filed on May 2, 2019; the benefit of priority of each of which is hereby claimed herein, and which applications and publication are hereby incorporated herein by reference in their entirety.

This disclosure relates generally to the application of radiotherapy, and in particular to gating the application of radiotherapy.

BACKGROUND

Radiotherapy uses ionising radiation to treat a human or animal body. In particular, radiotherapy is commonly used to treat tumours within the human or animal body. In such treatments, cells forming part of the tumour are irradiated by ionising radiation in order to destroy or damage them. However, in order to apply a prescribed dose of ionising radiation to a target location or target volume, such as a tumour, the ionising radiation will typically also pass through healthy tissue of the human or animal body. Therefore, radiotherapy has the desirable consequence of irradiating and damaging a target volume, but can also have the undesirable consequence of irradiating and damaging healthy tissue. In radiotherapy treatment, it is desirable to align the dose received by the target volume with a prescribed dose and to minimise the dose received by healthy tissue.

Modern radiotherapy treatment uses techniques to reduce the radiation dose to healthy tissue and thereby provide a safe treatment. For example, one approach to minimising a radiation dose received by healthy tissue surrounding a target volume is to direct the radiation towards the target volume from a plurality of different angles, for example by rotating a source of radiation around the patient by use of a rotating gantry. In this case, the angles at which radiation is applied are selected such that each beam of radiation passes through the target volume. In this way, a cumulative radiation dose may be built up at the target volume over the course of a treatment arc in which the radiation source rotates through a certain angle. However, since the radiation is applied from a plurality of different angles, the same, high, cumulative radiation dose is not built up in the healthy tissue because the specific healthy tissue the radiation passes through varies with angle. Therefore, a unit volume of the healthy tissue receives a reduced radiation dose relative to a unit volume of the target volume.

However, movement of a patient can affect the dose applied to different volumes of the patient's body. For example, movement of the patient can cause movement of unhealthy tissue such as a tumour and thus the dose applied to the target volume may be decreased and the dose applied to the healthy tissue may be increased. In other words, if a patient moves during or prior to radiotherapy treatment, this can cause a high cumulative dose to build up in a volume of healthy tissue instead of in a target volume. This can reduce the effectiveness of the radiotherapy for treating the target volume and can cause damage to otherwise healthy tissue.

There are various reasons why a patient may move during or prior to radiotherapy treatment. Gross or large-scale movements of a patient may include the patient shifting position. Discrete movements of the patient may include the patient coughing or sneezing. In some cases, large-scale movements may correspond to discrete movements. The patient may also undergo cyclical, physiological movement such as breathing. In attempts to accommodate these uncertainties, a planning target volume (PTV) may be defined. This may help to accommodate uncertainties related to the position of a target volume of unhealthy tissue and/or related to the delivery of a beam of radiation.

Known techniques for addressing movement of the subject include training a patient's breathing or asking the patient to hold their breath during radiotherapy treatment. In other known techniques, radiation may be selectively applied based on a position or movement of the patient. This is known as gating of the radiation beam. For example, in some prior systems, the movement of the patient may be sensed by any of a variety of known sensors. Radiation may be applied or not applied (i.e. the beam is gated) based on sensed movements or locations of the patient. For example, radiation may be applied when the patient or a part of the patient is within a certain range of locations based on the output of the sensor(s). One such approach can be performed using Ultrasound imaging and the Clarity VOICE software.

However, the definition of such ranges may be somewhat arbitrary. In particular, outputs of the sensors may not be directly linked to an actual movement or location of a tumour within the patient. In other words, it may be difficult to extrapolate from a sensed movement of a patient to determine whether, and to what extent, a location of a tumour within the patient has moved. This may result in inaccuracies in gating, which may cause irradiation of healthy tissue (due to radiation being applied when it should not be) and/or incomplete irradiation of a target volume (due to radiation not being applied when it should be).

Some prior approaches have used magnetic resonance (MR) imaging integrally with application of radiotherapy to determine whether a target volume is in a desired location. MR imaging information can be used to inform the gating so as to gate more accurately. The radiation may only be applied when a target volume is in a specific location, or within a certain tolerance of this specific location, as determined using the MR imaging. In other words, radiation may be applied or not applied based on geometric determinants, for example the coincidence or otherwise of an irradiated volume with a volume of a tumour.

However, the use of defined geometric volumes to inform when to apply radiation or not to apply radiation may not be as directly related to prescribed doses of radiation as is desirable. This may cause application of radiation doses that are not aligned with the prescribed doses for certain parts of a target volume. In addition, such approaches may not take into account locations of organs at risk (OAR) in determining when radiation should or should not be applied. For example, such approaches may cause radiation to be inadvertently applied to organs at risk that may move into a treatment volume. In addition, methods whereby a geometric volume and/or a tolerance are defined in the context of a treatment plan may be inaccurate or unclear. Subsequent changes to a dose gradient, i.e. to the distribution of the dose, may invalidate such arbitrarily defined geometrical parameters.

It would be advantageous to minimise the dose received by healthy tissue during radiotherapy treatment. It would also be advantageous to align the dose received by a target volume with an intended, e.g. prescribed, dose for the target volume more precisely. It would also be advantageous to increase the accuracy of radiotherapy treatment and thereby increase patient throughput.

The present invention seeks to address these and other disadvantages encountered in the prior art by providing improved application of radiotherapy.

SUMMARY

An invention is set out in the claims.

According to an aspect, there is provided a radiotherapy device comprising: a radiation source configured to apply radiation to a subject; and a controller configured to: determine an overlap between a defined volume of the subject and an isodose surface; and instruct the radiation source to halt application of the radiation based on the determination.

According to an aspect, there is provided a method of applying radiotherapy, the method comprising: applying radiation to a subject; determining an overlap between a defined volume of the subject and an isodose surface; and halting application of the radiation based on the determination.

According to an aspect, there is provided a radiotherapy device comprising: a radiation source configured to apply radiation to a target volume; and a controller configured to: determine whether less than a first threshold amount of the target volume is within a first isodose surface; and, in response to determining that less than the first threshold amount of the target volume is within the first isodose surface, instruct the radiation source to halt application of the radiation.

According to a further aspect, there is provided a method of applying radiotherapy, the method comprising: applying radiation to a target volume; determining whether less than a first threshold amount of the target volume is within a first isodose surface; and, in response to determining that less than the first threshold amount of the target volume is within the first isodose surface, halting application of the radiation.

According to a further aspect, there is provided a computer readable medium comprising computer executable instructions which, when executed by a processor, cause the processor to perform any of the disclosed methods.

According to a further aspect, there is provided a radiotherapy device comprising: a radiation source configured to apply radiation to a target volume; and a controller comprising computer executable instructions which, when executed by a processor, cause the processor to perform any of the disclosed methods.

According to a further aspect, there is provided a computer-implemented method comprising: determining an overlap between a defined volume of a subject and an isodose surface; and generating a computer-executable instruction for gating a radiation source based on the determination.

FIGURES

Specific embodiments are now described, by way of example only, with reference to the drawings, in which.

DETAILED DESCRIPTION

Instead of application of radiotherapy being gated based on geometric volumes, as in methods of the prior art, in presently disclosed methods application of radiotherapy is gated based on dose distributions. Isodose surfaces define volumes of a patient within which at least a particular dose will be received according to a treatment plan. These isodose surfaces are used to drive gating of the radiation beam, thereby providing a direct link between prescribed dosages/treatment plans and the gating of application of radiotherapy. This enables safer and more accurate radiotherapy treatment to be provided.

In the following, a method, apparatus and computer-readable medium for application of radiotherapy are provided. The apparatus may be configured to perform any of the method steps presently disclosed and may comprise computer executable instructions which, when executed by a processor, cause a processor to perform any of the method steps presently disclosed. Any of the steps that the apparatus is configured to perform may be considered as method steps of the present disclosure and may be embodied in computer executable instructions for execution by a processor. In the following, application of radiotherapy to a patient will be referred to in most detail in order to provide clarity of explanation. Such use of the term patient should not be interpreted to limit application of the present disclosure. The present disclosure provides means that can be used to apply radiotherapy to any subject. The terms patient and subject may be used interchangeably herein.

Figure 1:
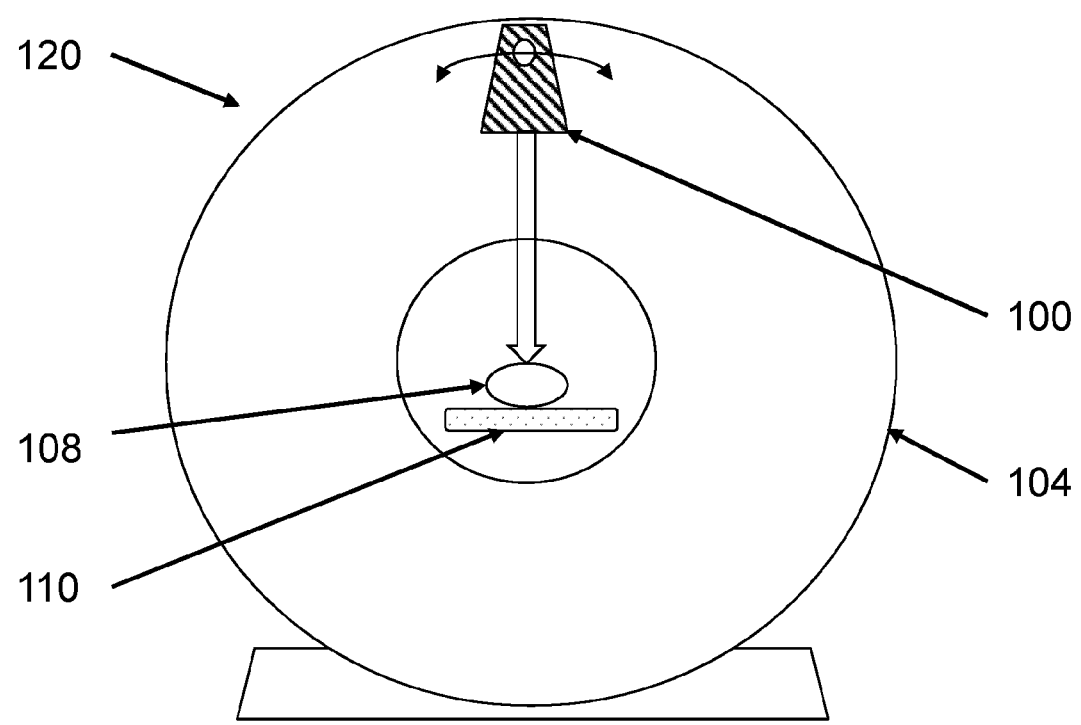
FIG. 1 depicts a radiotherapy device according to the present disclosure.

FIG. 1 depicts a radiotherapy apparatus according to the present disclosure. The Figure shows a cross-section through a radiotherapy device 120 comprising a radiation source 100 attached to a gantry 104. The radiotherapy device 120 may be an MR linac. Note: the MR imager is not shown. FIG. 1 also shows a subject 108 lying on a support surface 110. The radiation source 100 directs radiation towards the subject 108 from various angles around the subject 108 in order to spread out the radiation dose received by healthy tissue to a larger volume of healthy tissue while building up a prescribed dose of radiation at a target volume. As shown in FIG. 1, radiation may be emitted in a plane which is perpendicular to the axis of rotation of the radiation source 100.

A treatment delivery may comprise rotation of the radiation source 100 and application of radiation by the radiation source 100, for example according to a treatment plan. In some examples, the rotation may be continuous or pseudo-continuous such that a dose is applied from a continuous or pseudo-continuous range of angles. In other examples, the rotation may be to a plurality of discrete angles such that a dose is applied from a discrete series of angles. The rotation of the radiation source 100 may be predetermined according to a treatment plan. The treatment plan may comprise a prescribed dose (e.g. a clinically-prescribed dose) for the target volume. The prescribed dose may be a function of spatial coordinates, for example in one, two or three spatial dimensions. For example, the prescribed dose may vary spatially to account for concentrations of unhealthy tissue within the subject 108.

Figure 8:
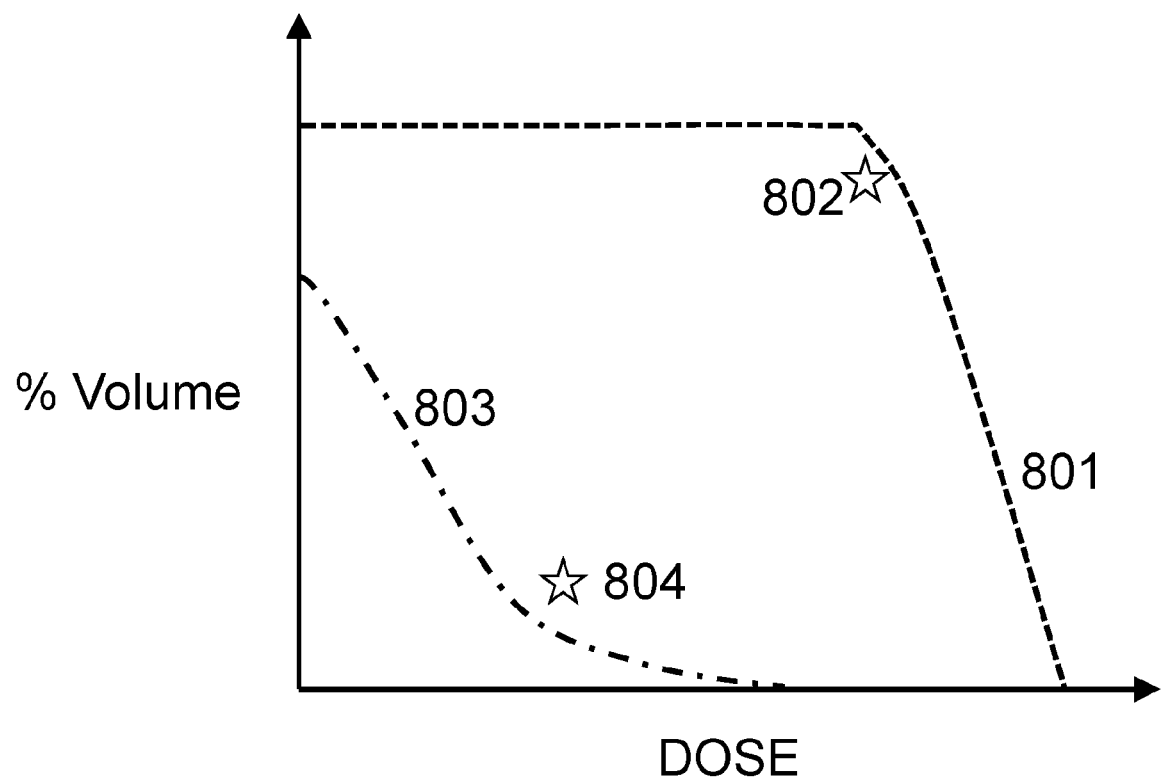
FIG. 8 depicts a dose volume histogram according to the present disclosure.

Planning a treatment delivery comprising a dose distribution involves solving a computational problem according to mathematical objective functions. It may be desired to deliver a dose above a threshold to a particular volume of a subject 108. This is a constraint that the solution to the computational problem must meet. The solution can provide positions of multi-leaf collimator leaves (which are moveable to limit the spatial extent of the radiation emitted by the radiation source 100), one or more time periods over which radiation is to be applied, angles around the gantry from which radiation is to be applied and/or intensity of the radiation beam. The treatment plan for a radiotherapy delivery may comprise this solution. The computational problem is solved using these degrees of freedom to meet the constraint that a specified dose must be applied to a specified volume. A further constraint may be imposed that a further specified dose must not be applied to a further specified volume. For example, it might be specified that no more than 20 Gy should be applied to 20% of an OAR such as a lung. In other words, the process of determining a treatment plan is driven according to constraints defining volumes that defined dose levels should be applied to, and/or by defining volumes that defined dose levels should not be applied to. This system of constraints is well known in the radiotherapy domain as dose volume constraints and each constraint can be visualised as a point on a Dose Volume Histogram, DVH (more correctly known as a cumulative Dose Volume Histogram) ref. FIG. 8. The cumulative dose to the voxels of a defined volume is represented as a curve on the DVH. For the target volume the curve has to pass above and to the right of the point and for a protected volume the curve has to pass to the left and below the point. The volumes on a DVH are normally represented as a portion or percentage of the volume on the vertical axis and the dose is represented on the horizontal axis. FIG. 8 shows an illustrative DVH with a curve 801 and constraint 802 for the target volume and a curve 803 and a constraint 804 for a protected volume. Since the problem of determining a treatment plan is defined in such terms, driving gating algorithms in the same terms provides a powerful improvement to delivery of radiotherapy. This provides a direct link between derivation of treatment plans and gating of a radiation beam, which provides more accurate radiotherapy delivery and conceptual overlap that may make radiotherapy delivery more understandable to a clinician and thereby improve radiotherapy planning.

Different subjects 108 may have different distributions or concentrations of unhealthy tissue. For example, different subjects 108 may have tumours of different sizes, different locations and/or different shapes. For this reason, a specific treatment plan may be determined for radiotherapy treatment of each subject 108 and/or each tumour. Determining the treatment plan may involve acquiring data for the subject 108. For example, MR imaging, computerised tomography (CT), ultrasound and/or other techniques may be used to derive images of structures inside a subject's body. Alternatively, or in addition, data may be provided based on clinical (e.g. internal) examinations. This can provide information on the distribution of a tumour, as well as information on the distribution of healthy tissue (e.g. OARs).

Figure 2:
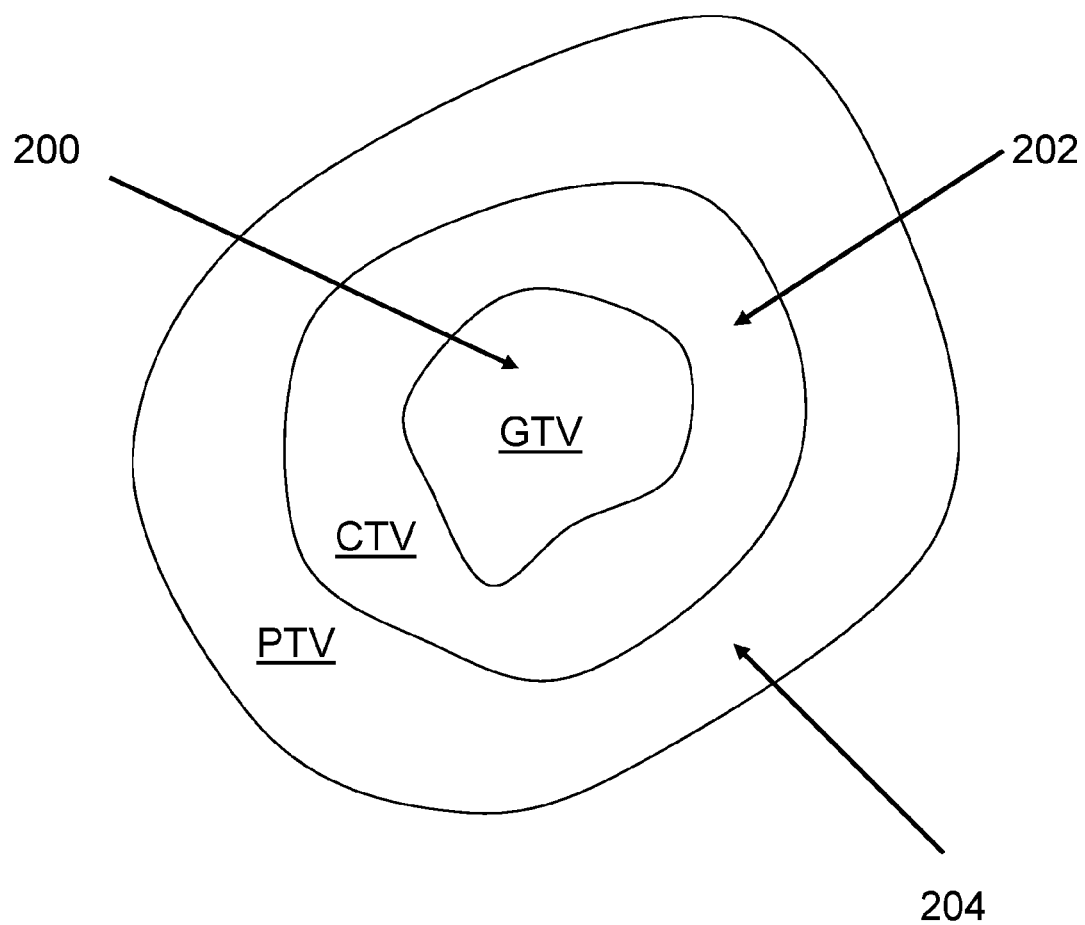
FIG. 2 depicts a schematic representation of defined volumes according to the present disclosure.

In determining a treatment plan, one or more volumes within the subject 108 may be defined. FIG. 2 depicts a schematic representation of such volumes according to the present disclosure. It will be appreciated that further and/or alternative volumes may be defined. A gross tumour volume (GTV) 200 may be defined as a gross, palpable, visible or clinically demonstrable location and extent of a malignant growth. A clinical target volume (CTV) 202 may be defined as a tissue volume that contains the GTV 200 as well as sub-clinical malignant disease which may be at risk and require treatment. The GTV 200 and the CTV 202 are therefore anatomical volumes within a subject that relate to a distribution of unhealthy tissue and/or to a probability of a distribution of unhealthy tissue. A planning target volume (PTV) 204 may be defined as a volume including the CTV 202 (and the GTV 200), as well as an additional margin to compensate for uncertainties and/or variations relating to the precision or setup of a radiotherapy beam and/or relating to positional uncertainty of the target volume and/or the protected volume. The PTV 204 is therefore a geometrical volume used to select beam arrangements in order to apply a prescribed dose to the CTV 202. In determining the above-mentioned volumes and the treatment plan, simulation of an instance of radiotherapy treatment may be used to provide treatment beam geometries appropriate for particular target volumes of the subject.

The GTV 200, CTV 202 and PTV 204 as depicted in FIG. 2 may correspond to the relative extent of these respective volumes in a certain plane, for example at a certain depth within a patient and at a certain orientation. At other depths and/or other orientations, the representations of the extents of these respective volumes may differ from those depicted in FIG. 2. The GTV 200, CTV 202 and PTV 204 as depicted in FIG. 2 provide a certain example of a distribution of unhealthy tissue, such as a tumour. It will be appreciated that other distributions may also occur and any such other distributions are considered to be within the present disclosure.

In some examples, the CTV 202 may extend beyond the GTV 200 by a different distance in different directions. In some examples, the extent of the CTV 202 may coincide with an extent of the GTV 200 at one or more points or in one or more directions. In some examples, the extent of the CTV 202 may differ from the extent of the GTV 200 by a constant distance. In some examples, the PTV 204 may extend beyond the GTV and/or the CTV 202 by a different distance in different directions. In some examples, the extent of the PTV 204 may coincide with an extent of the GTV 200 and/or the CTV 202 at one or more points or in one or more directions. In some examples, the extent of the PTV 204 may differ from the extent of the GTV 200 and/or the CTV 202 by a constant distance.

Based on the above considerations, and as part of the determination of the treatment plan, it may be determined that at least a certain prescribed dose of radiation should be applied to a certain target volume of the subject. The terms target volume and PTV 204 may be used interchangeably herein. A constraint may be imposed that the PTV 204 should receive a prescribed dose of radiation as part of a radiotherapy treatment. In order to account for incomplete overlap between the target volume and an actual volume in which the prescribed dose of radiation is applied, a first threshold amount may be defined. The first threshold amount may define a limit above which the application of radiation is considered acceptable and below which the application of radiation is not considered acceptable. The first threshold amount may be an absolute volume, or may be a percentage of the PTV 204, or may be based on a combination thereof. In some examples, the first threshold amount may be defined as 95% of the PTV 204 or the target volume, though this should not be understood as limiting the current disclosure.

Based on the above considerations, determining a treatment plan may include using dose management/calculation software to indicate distributions of expected doses. For example, a voxel (i.e. a discrete volume element of a subject) may be associated with an expected dose. An isodose surface may be defined as a surface joining points receiving an equal expected dose. In other words, all points on the isodose surface are expected to receive the same dose. For the purposes of illustration, such isodose surfaces may be thought of in a similar manner to altitude contours on geographic maps. Just as such contours can define points of constant altitude, isodose surfaces can define points of constant expected dose. As used herein, an isodose surface is a two-dimensional surface enclosing a volume. Furthermore, it will be understood that the dose on one side of the isodose surface is higher than on the other. When the phrase 'within an isodose surface' is used it means that the defined volume extends beyond the surface into the higher dose volume. While the Figures of the present disclosure depict two-dimensional views for ease of understanding, these may be understood as two-dimensional representations of three-dimensional features, for example the intersection of a three-dimensional volume with a two-dimensional plane.

The isodose surface may enclose a volume within which at least a particular dose will be received. A treatment plan may be determined with a 'top hat' dose profile such that the expected dose distribution is flatter in a target volume than at the immediate exterior of the target volume, so as to provide a relatively constant expected dose at the target volume and a relatively sharp drop-off in expected dose outside of the target volume.

According to the current disclosure, an overlap may be determined between a defined volume of the subject 108 and an isodose surface. Application of radiation may be halted based on the determination. The defined volume may be defined in a treatment plan. The defined volume may be predefined in advance of a treatment and/or may be updated based on measurements taken with the subject in a treatment position in order to increase accuracy. The defined volume may be updated during a radiotherapy treatment, for example based on MR imaging measurements and/or measurements of other sensors. The defined volume may comprise one or more volumes, for example one or more target volumes and/or one or more protected volumes. In some examples, the defined volume is a target volume. In some examples, the defined volume is a protected volume. One or more isodose surfaces may be used to make the determination in respect of one or more defined volumes. The overlap between the defined volume and the isodose surface may comprise a spatial overlap. For example, determining the overlap may comprise determining whether less than a threshold amount of a volume is within an isodose surface and/or determining whether at least a threshold amount (or more than a threshold amount) of a volume is within an isodose surface. In another implementation, methods and techniques disclosed herein may be applied to a two-dimensional defined region, a two-dimensional target region and/or a two-dimensional protected region, i.e. to two-dimensional areas.

Figure 3A:
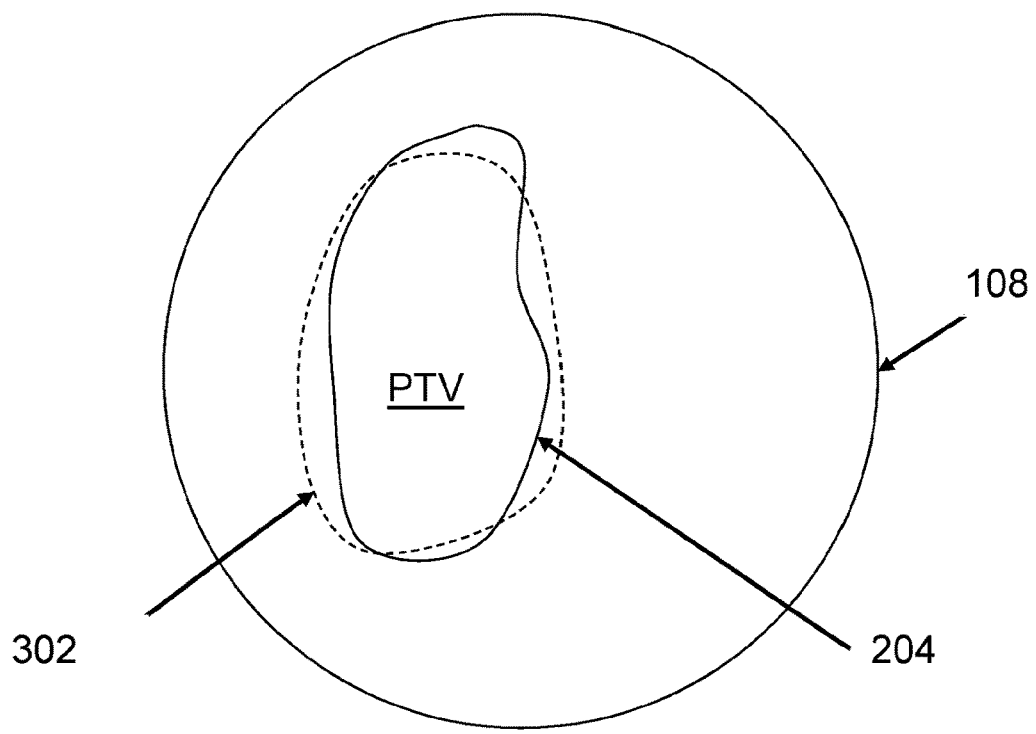
FIGS. 3a and 3b depict schematic representations of an isodose surface within a subject according to the present disclosure.

FIG. 3*a* depicts a schematic representation of an isodose surface according to the present disclosure. In a similar manner as applies to FIG. 2, FIG. 3*a* may depict the extent of surfaces in a given plane, e.g. at a given depth and a given orientation within a subject 108. A PTV 204 (as depicted with a solid line in FIG. 3*a*) may be defined within a subject 108 or within a certain part of a subject 108, for example within the head of a patient. The PTV 204 may correspond to the PTV 204 described in relation to FIG. 2, and may include the CTV 202 and GTV 200 (which are not depicted in FIG. 3*a* for ease of understanding). An isodose surface 302 (as depicted with a dashed line in FIG. 3*a*) may be defined based on a planned or expected dose associated with a treatment plan. The isodose surface 302 may depict an absolute level of dose, for example in units of Grays. Alternatively, the isodose surface 302 may depict a normalized dose relative to a maximum dose and/or a normalised dose relative to a dose at a defined point. While FIG. 3*a* depicts a single isodose surface 302 for ease of understanding, it will be understood that various isodose surfaces corresponding to different doses may be defined and depicted.

The isodose surface 302 depicted in FIG. 3*a* may correspond to a dose suitable for treating unhealthy tissue. It may be desirable for the isodose surface 302 to coincide with or include as much of the PTV 204 as possible. As explained above, a constraint may be imposed that a defined first threshold amount of the PTV 204 should receive a prescribed dose of radiation in the radiotherapy treatment. The isodose surface 302 may correspond to the prescribed dose. Therefore, a radiotherapy treatment setup may be suitable for treating unhealthy tissue in a certain target volume if at least a first threshold amount of the PTV 204 (e.g. 95% of the PTV 204) is within the isodose surface 302.

Figure 3B:
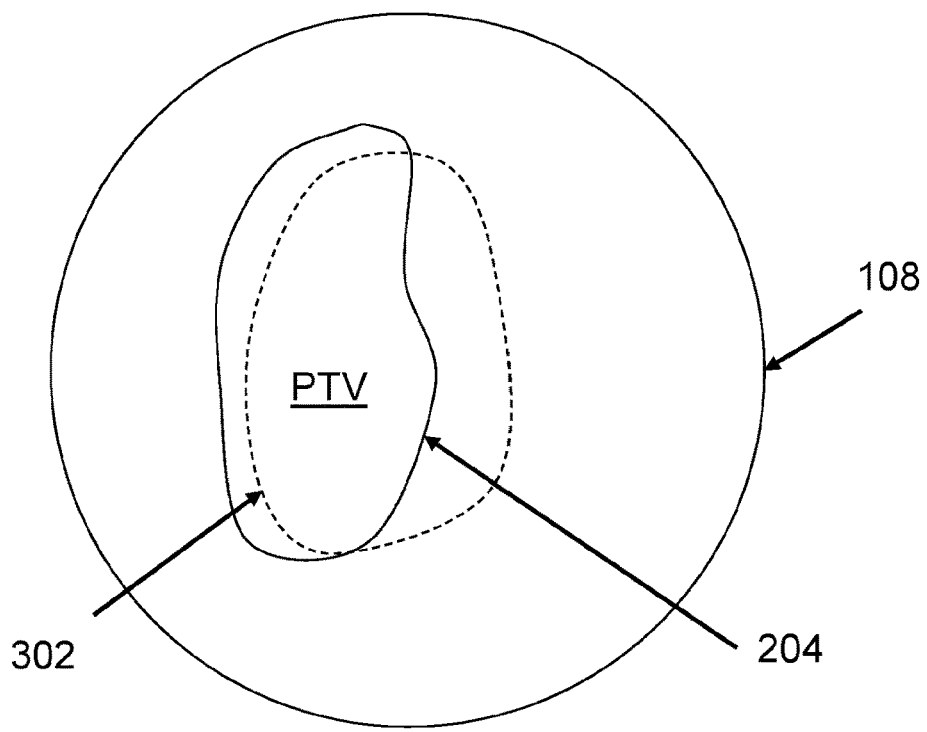

FIG. 3*b* depicts a schematic representation of the isodose surface of FIG. 3*a* after movement of the subject 108 and according to the present disclosure. As can be seen, in this example, the movement of the subject has resulted in a corresponding movement of the PTV 204. In some examples, the PTV 204 may move without movement of the subject 108 as a whole or the subject 108 may move as a whole without movement of the PTV 204. This may be caused, for example, by internal parts of a subject 108 moving relative to an external surface of the subject 108. Movement of the PTV 204 may be directly or indirectly related to movement of the subject 108 as a whole.

As shown in FIG. 3*b*, movement of the PTV 204 (optionally caused by movement of the subject 108) may cause a misalignment between the PTV 204 and the isodose surface 302. This may result in less than a first threshold amount of the PTV 204 being within the isodose surface 302. In this situation, the arrangement of the radiation beam may be unsuitable for treating the unhealthy tissue since a significant portion of the unhealthy tissue may not receive an appropriate (i.e. high enough) dose. In addition, the radiation beam may cause a greater than desirable portion of healthy tissue to receive an inappropriate (i.e. excessive) dose.

To address this, the current disclosure provides that the radiation source 100 is controlled to apply radiation when at least a first threshold amount of a target volume is within the isodose surface 302 (e.g. as shown in FIG. 3*a*), and to not apply radiation, for example to halt the application of radiation or gate the application of radiation, when less than the first threshold amount of the target volume is within the isodose surface 302 (e.g. as shown in FIG. 3*b*). Therefore, the present disclosure provides that volumes are defined and gating is driven based on isodose surfaces of dose distributions. This contrasts with prior approaches that gate application of radiation based on whether a target volume is within an arbitrarily-defined geometrical boundary. Thus, the present disclosure provides a direct link between prescribed doses and gating thresholds to enable more accurate application of radiotherapy treatment.

Application of radiation by the radiation source 100 in some time periods but not in others may be achieved by gating of a radiation beam emitted by the radiation source 100. The radiation source 100 may comprise an electron source and a radiofrequency (RF) field source. The electron source may provide a source of electrons which generate a radiation dose to be delivered to the subject 108, for example by impacting a target. The RF field source may electromagnetically accelerate the electrons to a desired velocity suitable for providing the radiation dose. The radiation source 100 may be gated by controlling the electron source to be on or off and/or by controlling the RF field source to be on or off. In this manner, application of a radiation dose by the radiation source 100 can be controlled according to desired parameters, for example based on isodose surfaces as described in the present disclosure.

While the movement depicted in FIG. 3b is a lateral movement, it will be appreciated that movement in any direction may cause misalignments and may result in less than a first threshold amount of a target volume, e.g. a PTV 204, being within an isodose surface 302. For example, when viewed in a certain plane, movement of the subject 108 away from the radiation source 100 may result in the isodose surface 302 appearing smaller than previously. Conversely, movement of the subject 108 toward the radiation source 100 may result in the isodose surface 302 appearing larger than previously.

Figure 4:
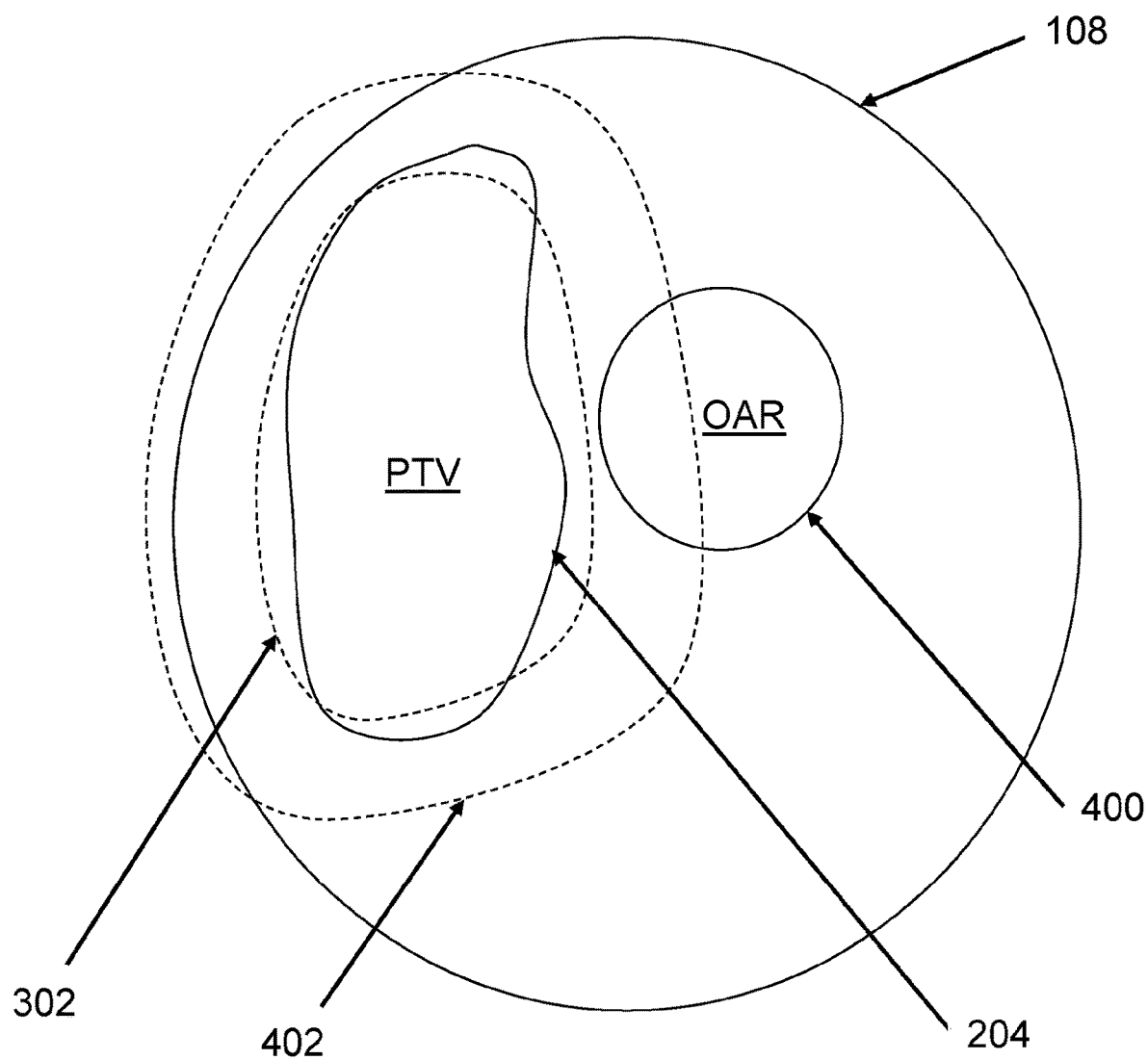
FIG. 4 depicts a schematic representation of multiple isodose surfaces and an organ at risk according to the present disclosure.

FIG. 4 depicts a schematic representation of multiple isodose surfaces 302, 402 and an organ at risk (OAR) 400 according to the present disclosure. Analogous to the extension of the CTV to the PTV to account for uncertainties, the OAR may be extended to the Planning Risk Volume or PRV. In other words, the PRV is a volume including the OAR 400, as well as an additional margin to compensate for uncertainties and/or variations relating to the precision or setup of a radiotherapy beam and/or relating to positional uncertainty of the OAR. As used herein, the terms protected volume and PRV may be used interchangeably. A protected volume may be a volume that it is desirable to protect (i.e. that it is desirable to limit application of radiation to). The depiction of the subject 108, the PTV 204 and the isodose surface 302 in FIG. 4 may correspond to the depiction of these features in FIG. 3a.

In FIG. 4, the isodose surface 302 may comprise a first isodose surface 302. A second isodose surface 402 may also be defined. The second isodose surface 402 may be defined similarly to the first isodose surface 302. All points on the second isodose surface 402 may be expected to receive a same second dose that may be different to a first dose expected to be received by all points on the first isodose surface 302. In some examples, the second isodose surface 402 may be the same as the first isodose surface 302. In some examples, a shape of the second isodose surface 402 may be similar to a shape of the first isodose surface 302 when depicted in a certain plane. However, the shapes of the first isodose surface 302 and the second isodose surface 402 may vary due to the beam geometries used. In other words, the variation of the dose distribution may vary non-linearly in different directions to different degrees. In other words, a dose gradient may be different in different directions. The dose gradient being different in different directions may entail that the target volume may move further in some directions than in other directions while still satisfying a defined threshold.

As shown in FIG. 4, the subject may comprise an OAR 400 and an associated protected volume. It may be desirable to limit the dose received by the protected volume. It may be desirable to apply a constraint that no more than a second threshold amount of the protected volume (e.g. 20% of the protected volume) should receive more than a certain dose, or a certain percentage of a maximum dose. This second threshold can be used in the gating algorithm alternatively or in addition to the first threshold used in respect of the PTV 204/target volume. In some instances, for example for a protected volume that is particularly susceptible to damage or that it is particularly important to protect, this second threshold may be set at zero (or at zero within measurement uncertainties). The radiation source 100 may be controlled to apply radiation when less than the second threshold amount of a protected volume is within the second isodose surface 402, and/or to not apply radiation, e.g. halt application of radiation or gate application of radiation, when more than the threshold amount of the protected volume is within the second isodose surface 402.

In some examples, a same threshold may be used in respect of the PTV 204 and in respect of the protected volume. In other words, the first threshold amount may correspond to the second threshold amount. In other examples, it may be desirable to set a lower threshold in respect of the protected volume than in respect of the PTV 204. In other words, the second threshold amount may be lower than the first threshold amount. This may increase the safety of the radiotherapy by further preventing damage to OARs 400.

It may be desirable to provide sensing, for example MR imaging, of a subject 108 in order to provide time-dependent information on locations of one or more isodose surfaces 302, 402 mapped onto a real-time location of a target volume and/or a protected volume. In this manner, an MR imaging device can constantly or at intervals update a location and/or a shape of the target volume, the isodose surfaces 302, 402 and/or the OARs 400 (for example in three dimensions). This provides benefits relative to defining a spatial volume once at the start of a treatment and not updating the spatial volume thereafter. In particular, use of MR imaging provides that real-time information may be incorporated that takes account of movements and/or changes of shape of a subject and/or a tumour so as to provide more accurate gating of application of a radiation beam. Therefore, the use of one or more isodose surfaces 302, 402 in driving the gating algorithm and the use of MR imaging to provide real-time geometric information both combine to provide more accurate beam gating and more accurate application of radiotherapy. The geometric information may comprise location information and/or shape information. In other words, the geometric information may indicate movement of a volume and/or changes in shape of a volume.

A method for determining the position of the defined volumes using MRI in real-time is defined by the following steps, one or more of which may be combined with another of the steps, rearranged or omitted:

Prior to treatment the defined volumes and isodose surfaces may be defined with respect to a previously acquired three-dimensional reference MRI. This will include a registration volume which contains sufficient image content that is relevant to the real time position of the target volume to enable robust real time image registration. At the start of the treatment a three-dimensional pre-treatment MRI may be acquired which is compared to the three-dimensional reference MRI. The defined volumes from the reference MRI can be updated using a rigid or non-rigid registration transform based on the relationship between the reference MRI and the pre-treatment MRI. During the treatment delivery multiple MRI two dimensional slices can be repetitively acquired, exemplary slice orientations to obtain three-dimensional information are two orthogonal slices, for example one in a sagittal plane and one in a coronal plane. At this time, two dimensional slices are used rather than volumes as they are faster. However, if technology permits fast enough three-dimensional imaging then this would be an option and is encompassed within the scope of the present disclosure. The intersection of the registration volume with the acquired slices may be used to extract relevant image content which can be successively registered against the three-dimensional pre-treatment MRI. These registration results can be used to further update the defined volumes and then compare them against the relevant isodose surface. So, the defined volumes can be updated just before treatment based on the three-dimensional pre-treatment MRI and then can be updated in real time based on the real time MRI slice imaging. The real time update can be a simple three-dimensional translation, a three-dimensional translation and rotation or a full deformation. The frequency of acquisition of these cine images is a significant part of the latency i.e. the time between the motion of the defined volume and the radiation beam being paused. An example of a relevant frequency for monitoring respiratory motion is between 3 and 10 images per second. The images can continue to be acquired and when the overlap conditions are met again the radiation beam can be re-enabled.

This 3D analysis is superior to 2D analysis as it correctly manages the motion of the defined volume for motion in any direction. A 2D approach may correctly manage motion within the particular 2D plane considered but may incorrectly manage motion components orthogonal to this 2D plane. Furthermore, motion components orthogonal to the 2D plane might compromise the in-plane motion. For example, the defined volume may be a sphere and the plane may, desirably, be through the middle of the sphere. The intersected area is then a circle with the same radius as the sphere. If the sphere moves orthogonal to the plane then the diameter of the intersected circle reduces. This will allow a greater movement of the defined volume within the plane over the isodose line before triggering the condition that causes gating of the treatment beam. If the target volume is small then it might even move out of the plane completely thus incapacitating the algorithm. The 3D analysis of defined volumes avoids such disadvantages and thereby enables more accurate and safer radiation therapy to be provided.

One or more assumptions may be made to simplify analysis of volumes and/or to make such analysis more efficient. For example, a reference treatment plan may define locations of various volumes of a subject, which may include a target volume and a protected volume. It may be assumed that the volumes of the subject move as rigid lumps. In other words, it may be assumed that a change in a location of the subject 108 causes a corresponding change in a location of the target volume and/or the protected volume (i.e. these are assumed to have moved by the same distance and/or in the same direction as the subject 108 as a whole). Such assumptions may be used in examples that do not use MR imaging.

Using MR imaging, it is possible to drive a gating algorithm based on one or both of the first threshold amount and the second threshold amount while taking account of real-time geometric information. In other words, a determination may be made whether less than a first threshold amount of an updated target volume is within a first isodose surface and/or whether at least a second threshold amount of an updated protected volume is within a second isodose surface. In other words, the determinations may be based on an updated target volume and/or an updated protected volume, the updates being based on the sensing, for example by the MR imaging device. Therefore, if at any time during a radiotherapy treatment, less than a first threshold amount of a target volume is within a first isodose surface 302 and/or more than a second threshold amount of a protected volume is within a second isodose surface 402, application of radiation by the radiation source 100 may be halted and/or gated.

In some examples, the treatment plan may be fixed before the start of radiotherapy treatment and may not vary during the radiotherapy treatment. In other examples, a treatment plan or a part thereof may be updated during a radiotherapy treatment. For example, a dose distribution may be updated in real time to provide isodose surfaces that vary in size and/or shape as a function of time. In these examples, a controller may determine whether one or more thresholds are satisfied, and thus whether to gate application of radiation, based on the isodose surface(s) 302, 402 and the location of the target volume and/or the protected volume at each of a series of time points. In other words, locations of a target volume, a protected volume, and/or an isodose surface 302, 402 may vary between different time points, but the controller may still determine whether one or more thresholds are satisfied at each time point and gate application of radiation accordingly.

A treatment plan may be determined in advance of a radiotherapy treatment, for example based on reference information for a subject 108 and/or a radiotherapy device 120. In order to improve the accuracy of a radiotherapy treatment, the treatment plan may be updated immediately prior to the radiotherapy treatment. This updated treatment plan may be based on the subject 108 being positioned in a treatment position in the radiotherapy device 120. Updating the treatment plan may comprise at least partially re-calculating the radiation dose to be delivered. This may cause the dose gradient to differ from the original treatment plan in one or more directions. Accordingly, one or more isodose surfaces 302, 402 may be updated in the updated treatment plan. The determinations using isodose surfaces 302, 402 as presently disclosed may be based on these updated isodose surfaces 302, 402 in order to further increase the accuracy of the presently disclosed methods.

While gating of radiation in response to less than a first threshold amount of a target volume being within a first isodose surface 302 has been referred to above, this may be considered to correspond to and/or include gating in response to at least one minus the first threshold amount of the target volume not being within the first isodose surface 302. Similarly, while gating of radiation in response to at least a second threshold amount of a protected volume being within a second isodose surface 402 has been referred to above, this may be considered to correspond to and/or include gating in response to less than one minus the second threshold amount of the protected volume not being within the second isodose surface 402. In these examples, the first and second threshold amounts may be expressed as percentages, proportions or fractions of the target volume and/or the protected volume.

The application of radiation by the radiation source 100 and/or the gating of the application of radiation may be controlled by the controller. The controller may be communicatively coupled to the radiation source 100. The controller may be configured to receive and/or update a treatment plan or information relating to a treatment plan. For example, the controller may be configured to receive geometric information for a target volume, a protected volume, and/or one or more isodose surfaces 302, 402. The controller may be communicatively coupled to a sensor configured to measure geometric information relating to the subject 108. The controller may comprise, or be described as, a computing device or a processor. The controller may be any machine capable of executing a set of instructions (sequential or otherwise) that specify actions to be taken by the radiotherapy device and the components thereof as described herein. The controller may be configured to generate one or more instructions and/or control signals for controlling one or more components of the radiotherapy device 120. For example, the controller may be configured to generate a computer-executable instruction or a control signal for gating a radiation source 100 and may be configured to transmit this computer-executable instruction or control signal to the radiation source 100.

Figure 5:
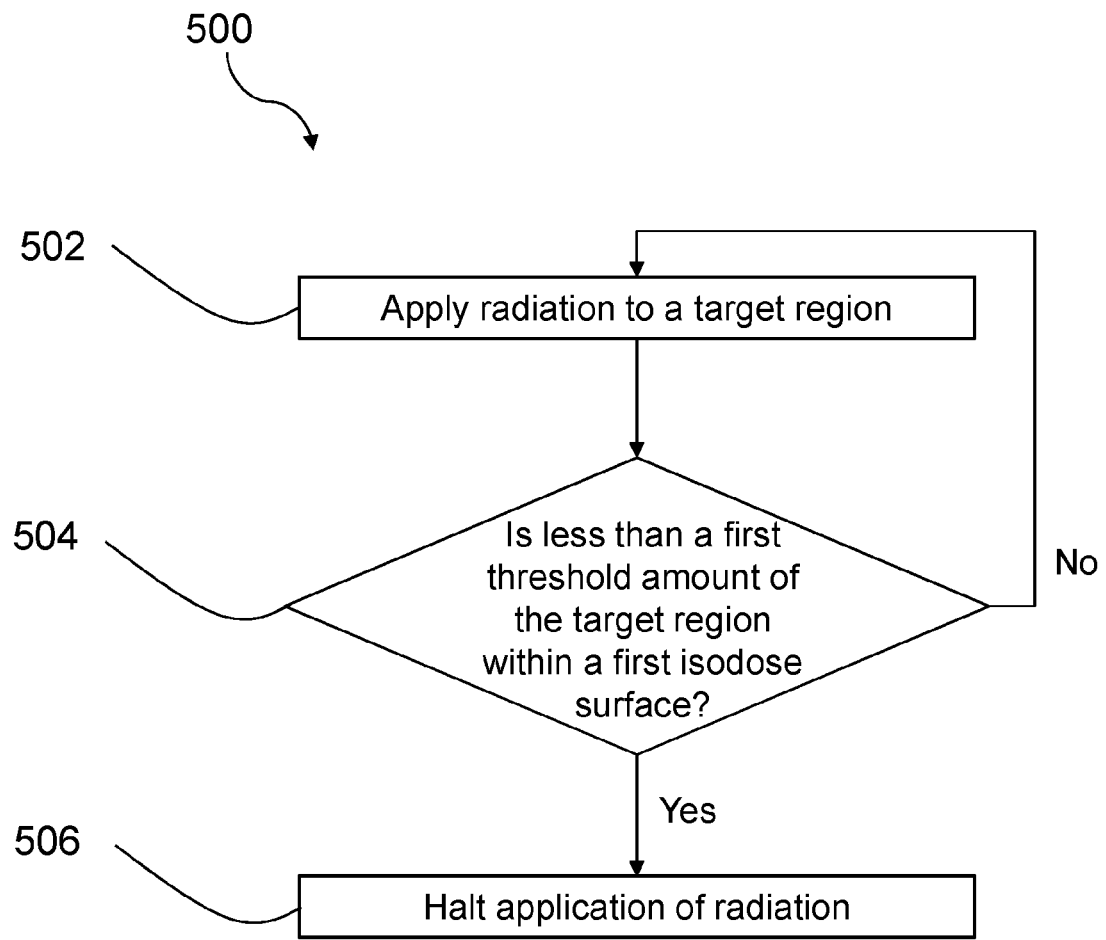
FIG. 5 depicts a method of controlling application of radiotherapy according to the present disclosure.

FIG. 5 depicts a method 500 of controlling application of radiotherapy according to the present disclosure. The method 500 may be performed using the radiotherapy device as presently disclosed.

In a step 502, radiation may be applied to a target volume. The radiation may be applied by a radiation source 100. The target volume may correspond to a PTV 204 and may be a target volume within a subject 108. The target volume may comprise unhealthy tissue, such as tumour. The target volume and/or the dose of radiation applied may be determined based at least in part on a treatment plan.

In a step 504, a determination may be made whether less than a first threshold amount of the target volume is within a first isodose surface 302. The first isodose surface 302 may be calculated or simulated based at least in part on a treatment plan. The determination may be made by a controller, which may receive geometric information for the target volume and/or information regarding the first isodose surface 302. The first threshold amount may be an absolute volume or may be a percentage of the target volume.

In response to a determination that not less than the first threshold amount of the target volume is within the first isodose surface 302, application of radiation to the target volume may be continued and/or resumed. In other words, the method may return to step 502.

In a step 506, in response to a determination that less than the first threshold amount of the target volume is within the first isodose surface 302, application of radiation to the target volume may be halted. In other words, the application of radiation may be gated based on the determination that less than the first threshold amount of the target volume is within the first isodose surface 302.

Figure 6:
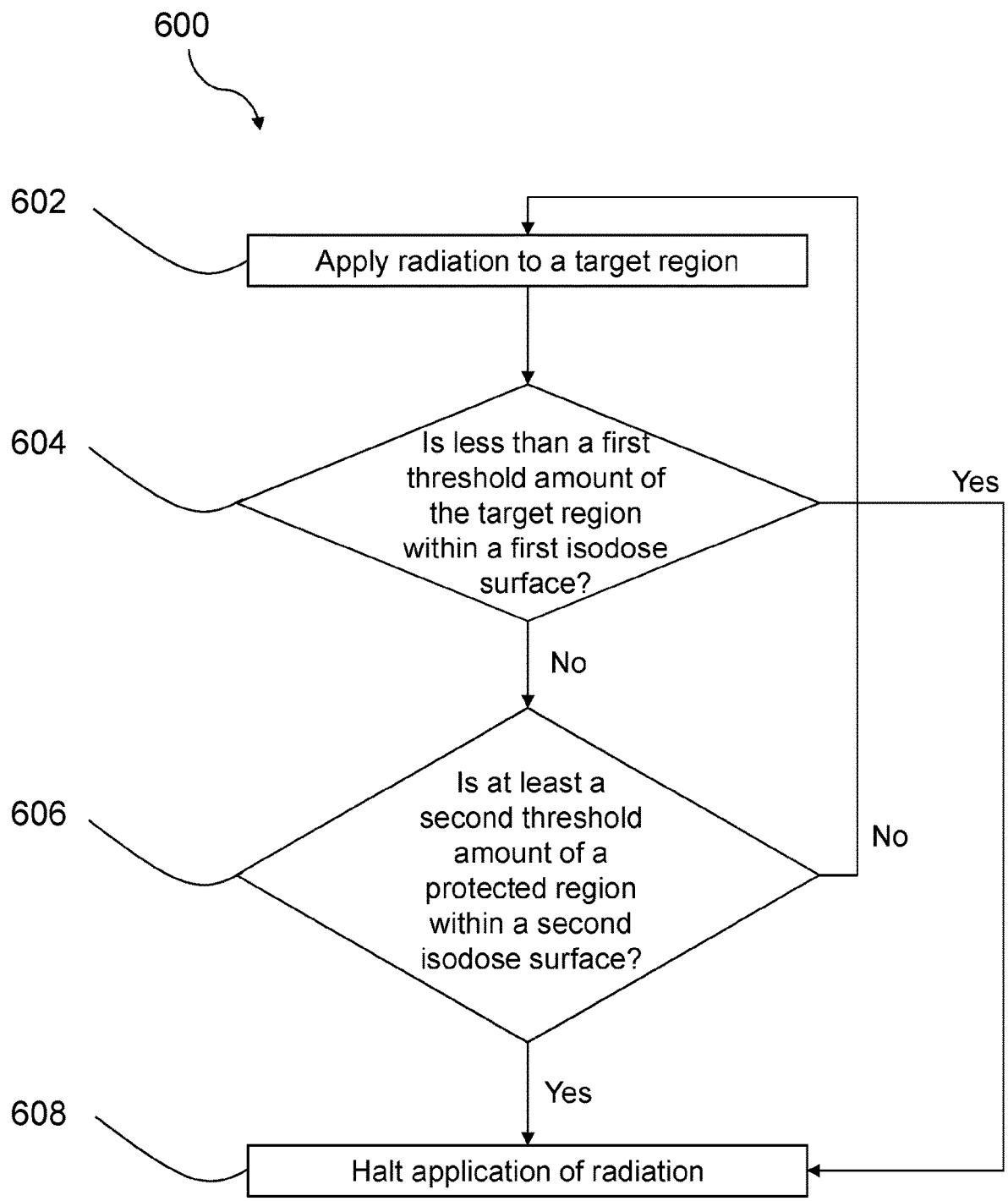
FIG. 6 depicts a further method of controlling application of radiotherapy according to the present disclosure.

FIG. 6 depicts a further method 600 of controlling application of radiotherapy according to the present disclosure. The method 600 may be performed using the radiotherapy device as presently disclosed.

In a step 602, radiation may be applied to a target volume. The step 602 may correspond to the step 502 as described above.

In a step 604, a determination may be made whether less than a first threshold amount of the target volume is within a first isodose surface 302. The step 604 may correspond to the step 504 as described above. In response to a determination that not less than the first threshold amount of the target volume is within the first isodose surface 302, the method may continue to a step 606. In response to a determination that less than the first threshold amount of the target volume is within the first isodose surface 302, the method may continue to a step 608.

In the step 606, a determination may be made whether at least a second threshold amount of a protected volume is within a second isodose surface 402. In some examples, a determination may instead be made whether more than the second threshold amount of the protected volume is within the second isodose surface 402. The second threshold amount may be an absolute volume or may be a percentage of the protected volume. In some examples, the second threshold amount may be equal to the first threshold amount. In some examples, the second threshold amount may be less than the first threshold amount. In some examples, the second threshold amount may be zero. The second isodose surface 402 may correspond to a second dose and the first isodose surface 302 may correspond to a first dose. In some examples, the second dose may be the same as the first dose. In other examples, the second dose may be less than the first dose.

In response to a determination that less than the second threshold amount of the protected volume is within the second isodose surface 402, application of radiation to the target volume may be continued and/or resumed. In other words, the method may return to step 602. In response to a determination that at least the second threshold amount of the protected volume is within the second isodose surface 402, the method may continue to the step 608.

In the step 608, in response to a determination that less than the first threshold amount of the target volume is within the first isodose surface 302 and/or a determination that at least the second threshold amount of the protected volume is within the second isodose surface 402, application of radiation to the target volume may be halted. In other words, the application of radiation may be gated based on the determination that less than the first threshold amount of the target volume is within the first isodose surface 302 and/or the determination that at least the second threshold amount of the protected volume is within the second isodose surface 402.

In the example depicted in FIG. 6, radiation may be halted if either less than a first threshold amount of a target volume is within a first isodose surface 302 or at least a second threshold amount of a protected volume is within a second isodose surface 402. In other examples, the step 604 may be excluded. In other words, a single determination may be performed based on the second threshold amount of the protected volume being within the second isodose surface 402. Application of radiation may be gated based at least in part on this determination. In such examples, there may be no target volume. For example, the method may not include determinations relating to any target volumes. In such examples, the presently disclosed methods may be thought of as providing safety mechanisms directed to preventing damage to protected volumes of a subject 108.

Figure 7:
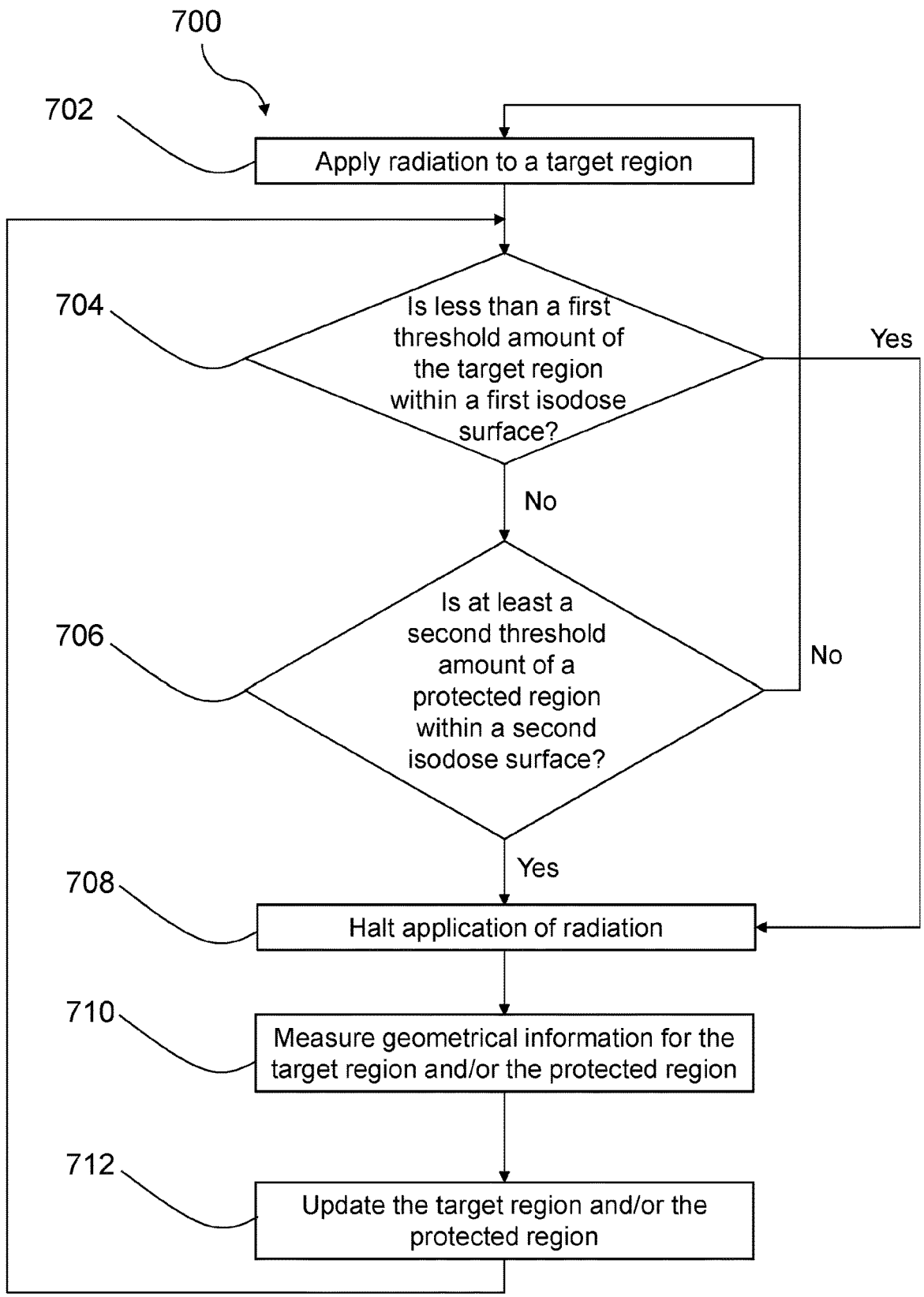
FIG. 7 depicts a further method of controlling application of radiotherapy according to the present disclosure.

FIG. 7 depicts a further method 700 of controlling application of radiotherapy according to the present disclosure. The method 700 may be performed using the radiotherapy device as presently disclosed.

In a step 702, radiation may be applied to a target volume. The step 702 may correspond to steps 502 and 602 as described above.

In a step 704, a determination may be made whether less than a first threshold amount of the target volume is within a first isodose surface 302. The step 704 may correspond to the steps 504 and 604 as described above. In response to a determination that not less than the first threshold amount of the target volume is within the first isodose surface 302, the method may continue to a step 706. In response to a determination that less than the first threshold amount of the target volume is within the first isodose surface 302, the method may continue to a step 708.

In the step 706, a determination may be made whether at least (or more than) a second threshold amount of a protected volume is within a second isodose surface 402. The step 706 may correspond to the step 606 as described above. In response to a determination that less than the second threshold amount of the protected volume is within the second isodose surface 402, application of radiation to the target volume may be continued and/or resumed. In other words, the method may return to step 702. In response to a determination that at least the second threshold amount of the protected volume is within the second isodose surface 402, the method may continue to the step 708.

In the step 708, in response to a determination that less than the first threshold amount of the target volume is within the first isodose surface 302 and/or a determination that more than the second threshold amount of the protected volume is within the second isodose surface 402, application of radiation may be halted or gated. The step 708 may correspond to the step 608 as described above. In some examples, the step 704 or the step 706 may be excluded. In other words, a single determination may be performed based on the first threshold amount of the target volume being within the first isodose surface 302 or based on the second threshold amount of the protected volume being within the second isodose surface 402. Application of radiation may be gated based at least in part on this determination.

In a step 710, geometric information for the target volume and/or the protected volume may be measured. The measuring may be performed by one or more sensors. The one or more sensors may comprise an MR imaging device. The geometric information may be transmitted to a controller, which may receive the geometric information. In some examples, the geometric information may be based upon a series of measurements corresponding to different spatial planes and/or different orientations and/or different time points.

In a step 712, the target volume may be updated to comprise an updated target volume and/or the protected volume may be updated to comprise an updated protected volume. The updated target volume and/or the updated protected volume may be based on the measured geometric information. The updated target volume and/or the updated protected volume may be determined by the controller. A change in the target volume and/or the protected volume, for example due to changes in the internal anatomy of the subject 108, may cause the updated target volume to be different to the target volume and the updated protected volume to be different to the protected volume.

Subsequent to step 712, the method may return to step 704. In one or more subsequent iterations of the method 700, the determination(s) of steps 704 and/or 706 may be based upon the updated target volume instead of the target volume and/or the updated protected volume instead of the protected volume. In this manner, gating of the application of radiation may be based on real-time overlaps between first isodose surfaces 302 and target volumes and/or between second isodose surface 402 and protected volumes. The method 712 may be repeated a plurality of times during a radiotherapy treatment, for example constantly or at a series of time intervals or at specific predetermined points during a radiotherapy treatment.

While the method depicted in FIG. 7 shows the measurement of geometric information (step 710) and the updating of the volumes (step 712) occurring after halting of application of radiation (step 708), step 710 and/or step 712 may occur following each iteration of step 704 and/or step 706. In other examples, step 710 and/or step 712 may be performed at time intervals, for example predetermined time intervals. Alternatively, or in addition, step 710 and/or step 712 may be performed following an integer number of occurrences of step 704 and/or step 706, and may be repeated following a further (same) integer number of such occurrences.

In presently disclosed methods, there may be multiple target volumes and/or multiple protected volumes. In other words, the determinations described herein may be made for each of several target volumes and/or for each of several protected volumes. Application of radiation may be halted if any of the determinations produce an undesirable result, for example if any of the thresholds are exceeded or not exceeded.

In presently disclosed methods, one or more of the determinations may be repeated for multiple threshold amounts. Each of the multiple threshold amounts may comprise a different proportion or absolute amount of a target volume or a protected volume, and may correspond to a different dose. For example, it may be determined whether more than 1% of a protected volume receives a dose of 40 Gray, i.e. is within an isodose surface 302, 402 corresponding to a dose of 40 Gray. It may further be determined whether more than 10% of the protected volume receives a dose of 30 Gray, i.e. is within an isodose surface 302, 402 corresponding to a dose of 30 Gray. Application of radiation may be halted if either of these determinations are satisfied (i.e. if an answer of 'true' is returned). Multiple threshold amounts may be used for the determinations relating to target volumes in a corresponding manner.

While the methods disclosed herein are presented in a certain sequential order, this should not be taken to limit the methods to the orders presented. One or more of the method steps may be omitted or rearranged. The various steps may be performed in different orders. Various steps may be performed at the same time or substantially the same time. Herein, references to events occurring substantially at the same time may refer to events at least partially overlapping in time and/or events occurring at the same time within measurement uncertainties.

The approaches described herein may be embodied on a computer-readable medium, which may be a non-transitory computer-readable medium. The computer-readable medium may carry computer-readable instructions arranged for execution upon a processor so as to cause the processor to carry out any or all of the methods described herein.

The term "computer-readable medium" as used herein refers to any medium that stores data and/or instructions for causing a processor to operate in a specific manner. Such storage medium may comprise non-volatile media and/or volatile media. Non-volatile media may include, for example, optical or magnetic disks. Volatile media may include dynamic memory. Exemplary forms of storage medium include, a floppy disk, a flexible disk, a hard disk, a solid state drive, a magnetic tape, or any other magnetic data storage medium, a CD-ROM, any other optical data storage medium, any physical medium with one or more patterns of holes, a RAM, a PROM, an EPROM, a FLASH-EPROM, NVRAM, and any other memory chip or cartridge.

The present disclosure enables clinically-prescribed dosage constraints to be used to gate a radiotherapy beam. This provides a more direct link between dosage constraints and gating of the radiotherapy beam. The present disclosure thereby is more intuitive for a user as treatment planning is performed in terms of dose objectives rather than in terms of arbitrarily defined geometrical volumes. Moreover, this direct link between isodose surfaces and gating of the radiotherapy beam provides more accurate radiotherapy treatment in respect of unhealthy tissue and safer radiotherapy treatment in respect of organs at risk.

It is to be understood that the above description is intended to be illustrative, and not restrictive. Many other implementations will be apparent to those of skill in the art upon reading and understanding the above description. Although the present disclosure has been described with reference to specific example implementations, it will be recognized that the disclosure is not limited to the implementations described, but can be practiced with modification and alteration within the scope of the appended claims. Accordingly, the specification and drawings are to be regarded in an illustrative sense rather than a restrictive sense. The scope of the disclosure should, therefore, be determined with reference to the appended claims, along with the full scope of equivalents to which such claims are entitled.

The invention claimed is:

1. A A radiotherapy device comprising:
    a radiation source configured to apply radiation to a subject; and
    a controller configured to:
        determine an overlap between a defined volume of the subject and an isodose surface; and
        instruct the radiation source to halt application of the radiation based on the determination;
    wherein the radiation source is configured to apply the radiation to a target volume, wherein the defined volume comprises the target volume and a protected volume, and wherein the controller being configured to determine the overlap between the defined volume and the isodose surface includes the controller being configured to at least one of:
        determine whether less than a first threshold amount of the target volume is within a first isodose surface; or
        determine whether less than a first threshold amount of the target volume is within a first isodose surface and determine whether more than a second threshold amount of the protected volume is within a second isodose surface.

2. The radiotherapy device according to claim 1, comprising a sensor configured to:
    measure geometric information for at least one of the target volume or the protected volume; and
    transmit the geometric information to the controller;
    wherein the controller is further configured to:
    receive the geometric information from the sensor; and
    update at least one of the target volume based on the geometric information to determine an updated target volume or the protected volume based on the geometric information to determine an updated protected volume.

3. The radiotherapy device according to claim 2, wherein the controller is further configured to:
    instruct the radiation source to halt application of the radiation based on at least one of a determination that less than the first threshold amount of the updated target volume is within the first isodose surface or a determination that more than the second threshold amount of the updated protected volume is within the second isodose surface.

4. The radiotherapy device according to claim 2, wherein the controller is further configured to:
    instruct the radiation source to apply radiation based on at least one of a determination that at least the first threshold amount of the updated target volume is within the first isodose surface or a determination that less than the second threshold amount of the updated protected volume is within the second isodose surface.

5. The radiotherapy device according to claim 2, wherein the sensor is a magnetic resonance imaging device.

6. The radiotherapy device according to claim 1, wherein the first threshold amount is larger than the second threshold amount.

7. A radiotherapy device according to claim 1, wherein the first isodose surface corresponds to a first dose, the second isodose surface corresponds to a second dose, and wherein the first dose is larger than the second dose.

8. A radiotherapy device according to claim 1, wherein at least one of: the first isodose surface comprises an updated first isodose surface or the second isodose surface comprises an updated second isodose surface, wherein at least one of the updated first isodose surface or the updated second isodose surface is determined by the controller based at least in part on measurements taken with the subject in a treatment position.

9. The radiotherapy device according to claim 1, wherein at least one of: the first threshold amount comprises a first plurality of threshold amounts, and the first isodose surface comprises a first plurality of isodose surfaces, each respective isodose surface corresponding to a different dose of radiation, or wherein the second threshold amount comprises a second plurality of threshold amounts, and the second isodose surface comprises a second plurality of isodose surfaces, each respective isodose surface corresponding to a different dose of radiation, and wherein the controller is further configured to, for each threshold amount of the first plurality of threshold amounts and each isodose surface of the first plurality of isodose surfaces:
    determine whether less than a respective threshold amount of the target volume is within a respective isodose surface; and
    based on determining that less than the respective threshold amount of the target volume is within the respective isodose surface, instruct the radiation source to halt application of the radiation;
    or, for each threshold amount of the second plurality of threshold amounts and each isodose surface of the second plurality of isodose surfaces:
    determine whether more than a respective threshold amount of the protected volume is within a respective isodose surface; and
    based on determining that more than the respective threshold amount of the protected volume is within the respective isodose surface, instructing the radiation source to halt application of the radiation.

10. A computer-implemented method comprising:
    determining an overlap between a defined volume of a subject and an isodose surface; and
    generating a computer-executable instruction for gating a radiation source based on the determination, wherein the defined volume comprises at least one of a target volume or a protected volume, and wherein determining the overlap between the defined volume and the isodose surface comprises at least one of:
        determining whether less than a first threshold amount of the target volume is within a first isodose surface; or
        determining whether less than a first threshold amount of the target volume is within a first isodose surface and determining whether more than a second threshold amount of the protected volume is within a second isodose surface.

11. The computer-implemented method according to claim 10, further comprising:
  measuring geometric information for at least one of the target volume or the protected volume; and
  updating at least one of the target volume based on the geometric information to determine an updated target volume or the protected volume based on the geometric information to determine an updated protected volume.

12. The computer-implemented method according to claim 11, further comprising:
  instructing halting application of radiation based on at least one of a determination that less than the first threshold amount of the updated target volume is within the first isodose surface or a determination that more than the second threshold amount of the updated protected volume is within the second isodose surface.

13. The computer-implemented method according to claim 11, further comprising:
  instructing application of radiation based on at least one of a determination that the first threshold amount of the updated target volume is within the first isodose surface or a determination that less than the second threshold amount of the updated protected volume is within the second isodose surface.

14. The computer-implemented method according to claim 11, wherein the measuring is performed using magnetic resonance imaging.

15. The computer-implemented method according to claim 10, wherein at least one of the first threshold amount is larger than the second threshold amount or the first isodose surface corresponds to a first dose, the second isodose surface corresponds to a second dose, and the first dose is larger than the second dose.

16. The computer-implemented method according to claim 10, wherein at least one of the first isodose surface comprises an updated first isodose surface or the second isodose surface comprises an updated second isodose surface, and wherein at least one of the updated first isodose surface or the updated second isodose surface is based at least in part on measurements taken with the subject in a treatment position.

17. The computer-implemented method according to claim 10, wherein at least one of the first threshold amount comprises a first plurality of threshold amounts, and the first isodose surface comprises a first plurality of isodose surfaces, each respective isodose surface corresponding to a different dose of radiation, or wherein the second threshold amount comprises a second plurality of threshold amounts, and the second isodose surface comprises a second plurality of isodose surfaces, each respective isodose surface corresponding to a different dose of radiation, and wherein the method comprises, for each threshold amount of the first plurality of threshold amounts and each isodose surface of the first plurality of isodose surfaces:
  determining whether less than a respective threshold amount of the target volume is within a respective isodose surface; and
  based on determining that less than the respective threshold amount of the target volume is within the respective isodose surface, instructing the radiation source to halt application of the radiation;
  or for each threshold amount of the second plurality of threshold amounts and each isodose surface of the second plurality of isodose surfaces:
  determining whether more than a respective threshold amount of the protected volume is within a respective isodose surface; and
  based on determining that more than the respective threshold amount of the protected volume is within the respective isodose surface, instructing the radiation source to halt application of the radiation.

18. A non-transitory computer readable medium comprising computer executable instructions which, when executed by a processor, cause the processor to:
  determine an overlap between a defined volume of a subject and an isodose surface; and
  generate a computer-executable instruction for gating a radiation source based on the determination;
  wherein the radiation source is configured to apply the radiation to a target volume, wherein the defined volume comprises the target volume and a protected volume, and wherein causing the processor to determine the overlap between the defined volume and the isodose surface includes the causing the processor to:
  determine whether less than a first threshold amount of the target volume is within a first isodose surface; and
  determine whether more than a second threshold amount of the protected volume is within a second isodose surface.

* * * * *